United States Patent [19]

Barry et al.

[11] Patent Number: 5,038,779
[45] Date of Patent: Aug. 13, 1991

[54] THERAPEUTIC GARMENT

[76] Inventors: Kevin P. Barry, 24792 Daphne West, Mission Viejo, Calif. 92691; Dean J. Drulias, 2024 MacArthur, Rancho Palos Verdes, Calif. 90732

[21] Appl. No.: 625,110

[22] Filed: Dec. 10, 1990

[51] Int. Cl.$^5$ .......................... A61F 7/00; A61F 5/02; A41D 1/04; A41D 27/20
[52] U.S. Cl. .................... 128/402; 128/403; 128/399; 128/78; 272/119; 2/102; 2/247; 2/267
[58] Field of Search ................. 128/78, 399, 402, 403; 272/119; 2/102, 247, 267

[56] References Cited

U.S. PATENT DOCUMENTS

| | | |
|---|---|---|
| 447,103 | 2/1891 | Cussen ................................. 2/247 |
| 2,008,783 | 7/1935 | Ceridis ................................. 2/247 |
| 3,074,250 | 1/1963 | Everett . |
| 3,296,819 | 1/1967 | Gough . |
| 3,452,554 | 7/1969 | Smith . |
| 3,476,102 | 11/1969 | Sarnoff . |
| 3,643,463 | 2/1972 | Friedlander et al. . |
| 3,802,215 | 4/1974 | Rowe . |
| 3,950,789 | 4/1976 | Konz et al. . |
| 4,190,054 | 2/1980 | Brennan ............................. 128/402 |
| 4,253,313 | 3/1981 | Rowe . |
| 4,382,302 | 5/1983 | Watson ................................. 2/102 |
| 4,586,506 | 5/1986 | Nangle ............................. 128/403 |
| 4,949,401 | 8/1990 | Kinsey, Jr. ............................. 2/102 |
| 4,989,267 | 2/1991 | Watson ................................. 2/102 |

FOREIGN PATENT DOCUMENTS 289955  5/1928  United Kingdom ................... 2/247

*Primary Examiner*—Richard J. Apley
*Assistant Examiner*—Karen G. Horowitz
*Attorney, Agent, or Firm*—Jeffrey G. Sheldon

[57] ABSTRACT

A therapeutic garment is adapted to be worn on a human torso for therapeutic treatment of back pain. The garment has at least one pocket in the lower back section of the garment. The pocket is capable of removably receiving a packet to create a thermal change in the pocket. The distance between the pocket and the upper back section of the garment is adjustable so that the garment can be used by persons of different torso length.

12 Claims, 2 Drawing Sheets

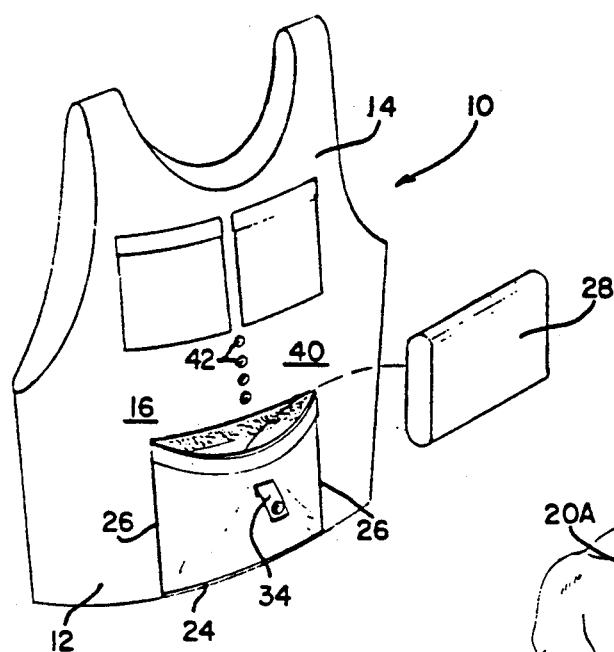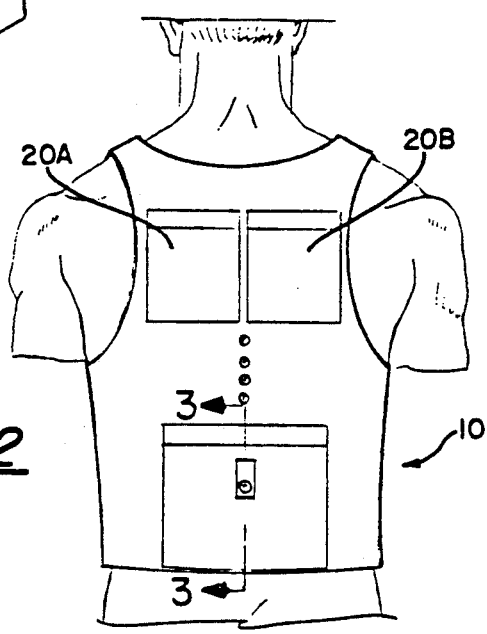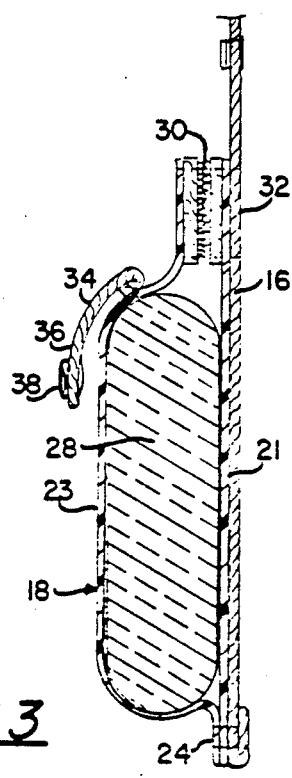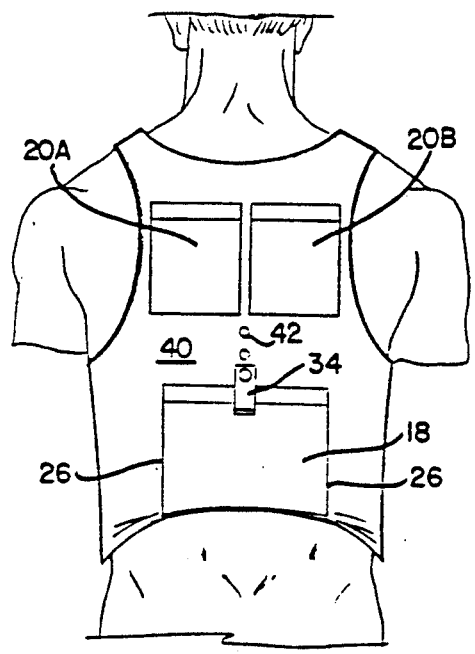

THERAPEUTIC GARMENT

BACKGROUND

The present invention is directed to a garment particularly suitable for therapeutic treatment of injuries to the upper and lower back.

Back pain due to injuries to the back are among the most common of debilitating conditions suffered by humans. It is well known that it is desirable to apply heat and/or cooling to back injuries. However, it is extremely difficult to do so, particularly for active working people. It is impractical to apply a heating pad or an ice pack to one's back while working in a factory or working in an office.

A variety of garments have been proposed for applying heat or cooling to humans, but they all suffer from disadvantages. Garments designed to locally vary the temperature of the human body are described in U.S. Pat. Nos. 3,074,250; 3,296,819; 3,476,102; and 3,950,789. Some of these garments are bulky and cannot be worn during activities such as work, athletics, and recreation. Another disadvantage of many prior garments is that they need to be provided in different sizes, depending upon the size of the individual wearing a garment. For example, if heat or cooling is required in the lower back, a garment with a pocket located to cool the lower back of a tall person, if used on a short person, would end up cooling the derriere.

Accordingly, there is a need for a garment that provides therapeutic heat or cold treatment to the individual wearing the garment, where the garment can be worn by individuals of different sizes, and can be worn during daily activities.

SUMMARY

A garment that meets this need is adapted to be worn on a human torso for therapeutic treatment of back pain. The garment comprises an inner layer of material forming a wearable shirt having a lower back section and an upper back section. The garment includes an outer layer of material forming a pocket in the lower back section of the garment. The pocket is capable of removably receiving a packet to create a thermal change, i.e., cooling or heating. It also provides lumbar support. The inner layer of material of the pocket is heat conductive so that the packet can alter the temperature of the lower back of the user of the garment.

Preferably, the garment has at least one upper back pocket in the upper back section, and preferably two upper back pockets side by side. Each upper back pocket is capable of removably receiving a packet to create a thermal change in the pocket.

Preferably the packets can either be heated or cooled, depending upon whether the injury needs heating or cooling.

The garment also includes means for adjusting the distance between the pocket and the upper back section of the garment so that the garment can be used by persons of different torso length.

A variety of means for adjusting the distance between the pocket and the upper back section of the garment can be used. For example, the adjusting means can comprise a strap, a first attachment device serving to attach the strap to the pocket at a first location, and a second attachment device serving to attach the strap to the garment at a second location, the second location being above the pocket. The adjusting means allows the distance between the first location and the second location to be adjusted. For example, the strap can be fixedly attached to the pocket so that the first location is not adjustable, and the second attachment device can comprise a snap fastener, a male portion on the strap and a plurality of female portions at different elevations on the garment. Alternately, a plurality of the male portions of a fastener system can be used with a plurality of the female portions or with just one female portion.

In another version of the invention, the means for adjusting the height of the lower packet can comprise first attachment means extending across the width of the pocket, and at least two vertically spaced apart second attachment means extending across the width of the back of the garment at locations above the lower pocket. The first attachment means is capable of being attached to any one of the second attachment means. An advantage of using laterally extending attachment means is that better support is provided for the packet in the lower pocket.

Preferably the outer layer is impervious to water in the location of the pockets to avoid wetting of the user's outer garments due to condensation on a cooling packet.

Preferably each pocket has means for releasably closing the pocket such as a VELCRO brand hook and loop fastener system.

DRAWINGS

These and other features, aspects and advantages of the present invention will become better understood from the following description, appended claims, and accompanying drawings where:

FIG. 1 is a rear perspective view of a therapeutic garment according to the present invention;

FIG. 2 is a rear elevation view of an individual wearing a garment having features of the present invention, a pocket in the lower back portion of the garment being in its lowermost position;

FIG. 3 is a side sectional view of the garment of FIG. 2 taken on line 3—3 in FIG. 2;

FIG. 4 is a rear elevation view similar to that of FIG. 2 wherein the pocket is in a raised position.

DESCRIPTION

Figure 5:
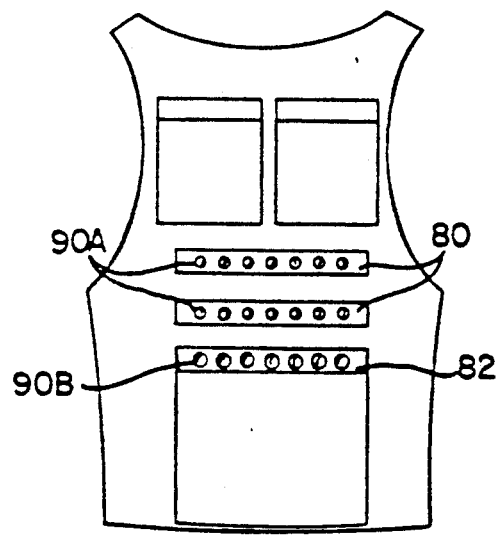
FIG. 5 is a rear elevation view of another version of a therapeutic garment according to the present invention.

A garment 10 according to the present invention is in the form of a pullover, sleeveless vest or a t-shirt. It is sized to fit over the torso of a user, and is shown in such a position in FIGS. 2 and 4. The garment 10 can be provided with buttons or a zipper so it is not necessarily a pullover device. Moreover, it can be provided with sleeves. The garment 10 is designed to be worn under every day clothing so that it can be worn whatever the occasion.

The garment 10 comprises a lower back portion 12 and an upper back portion 14. The garment 10 is formed from fabric 16 and is provided with a plurality of pockets, which in the version shown in the drawings, comprise a lower back pocket 18, and two upper back pockets 20A and 20B. The upper back pockets 20A and 20B are side by side. The upper back pockets are located in the region where upper back pain is often experienced.

The pockets are self-contained, being formed from a single piece of material, folded over to form an inner layer 21 and an outer layer 23. Each of the pockets is rectangular and is stitched to the garment fabric 16 along a bottom edge 24 and upwardly extending side edges 26.

Each pocket is adapted to hold one or more thermal control packets 28. After a packet is inserted in a pocket, the upper edge of that pocket is closed by suitable fastening means. In the embodiment illustrated, the upper edge of the outer layer 23 of each pocket is provided with a strip 30 of a hook and loop fastener such as Velcro brand fastener which can be removably secured to a complementary strip 32 which is attached to the inner layer 21. Alternatively the pockets can be fastened by such means such as flaps, buttons, or a zipper.

The garment fabric 16 needs to be sufficiently strong to accommodate the weight of the packet(s). In addition, preferably the garment fabric 16, and particularly the portions of the fabric 16 at the pockets, is made of a suitable material such as wool or cotton, capable of absorbing the moisture of the wearer of the garment. Such a material is preferable to a non-absorbent material such as Dacron, Nylon, or the like since the fabric when it does become moist becomes a better heat transfer medium than when dry. Alternatively the inner fabric 16 can be made of a blend of natural and synthetic fibers, i.e., a blend of cotton and synthetic fibers (referred to as cotton poly INTERLOCK). Another suitable material for at least portions of the garment body is LYCRA brand elastic cotton material.

The pockets can be made of any strong material sewn or otherwise fastened to the fabric 16. Preferably the pockets are made of a water-impervious or resistant material such as a synthetic fiber, so that when a cooling packet is used, moisture that condenses on the cooling pocket does not soak through the garment 10 and become visible on the overlaying garments. A suitable material is SUPPLEX (trademark) water resistant material.

The packet 28 can be of a type that provides cooling, provides heating, or one that can provide both heating or cooling, depending upon the treatment of the packet before it is inserted in the garment. A suitable cooling packet is of the type that is available for sports injuries. Even when the packet is cooled in the freezer, it remains flexible. Such a packet is available under the trademark PRO-TEMP CP from Meyer Distributing Co., Inc., of Upland, California. It is cooled to the desired temperature merely by placing it in a freezer of a home refrigerator. A suitable packet that can be either heated or cooled is one available from Jack Frost Laboratories, Incorporated of Fort Pierce, Fla. under catalog number 0737 as described in U.S. Pat. No. 4,756,311. These packets can be cooled by placement in a freezer, or alternatively can be heated to provide heat therapy by placing and heating them in a microwave oven.

An important feature of the present invention is the capability of adjusting the position of the lower back pocket 18. This allows the application of therapy to the specific portion of the lower back that is in pain, and also allows the garment 10 to be worn by individuals of different torso lengths.

In the version of the invention shown in FIGS. 1-4, a short strap 34 is secured such as by sewing to the outer layer 23 of the lower back pocket 18. The strap 34 has on its inside surface 36 the male portion 38 of a snap fastener assembly. On the outside surface 40 of the garment above the lower back pocket 18 are a plurality of the female portion 42 of the snap fastener assembly. The female portions 42 are situated one above the other. By snapping the male portion 38 into a selected one of the female portions 42, the distance between the lower back pocket and the upper back pockets 20A and 20B can be varied with the net effect of lowering and raising the lower back pocket 18. As shown in FIG. 2, when the strap 34 is not connected to any of the female portions of the fastener assembly, the lower back pocket 18 is in its lowermost position. As shown in FIG. 4, when the strap 34 is fastened to a female portion 42, the lower back pocket 18 is raised.

A variety of techniques can be used for adjusting the position of the lower pockets and the upper pockets. For example, rather than using snap fasteners, a button hole can be placed in the strap 34 for attachment to any one of a plurality of buttons. Further, the strap 34 can be fixedly attached to the garment 16 above the pocket 18, and the plurality of fasteners can be provided on the pocket 18 at various elevations. Another technique for attaching the strap is to use VELCRO brand hook and loop fasteners, with one portion of the fastener attached to the strap and another portion attached as a vertically oriented strip on the outer lower surface 40 of the garment material 16

If desired, the garment 10 can be provided with belts or straps for holding the therapeutic packets close against the user for good heat conductivity.

FIG. 5 shows an alternate version of a lower back pocket adjustment system. In this version of the invention, the garment 10 is provided with a plurality of parallel, spaced apart, horizontal fastener strips 80 across a substantial portion of the width of the back of the garment. These strips 80 cooperate with at least one corresponding strip 82 on the top section of the lower pocket 18. The strip 82 extends across a substantial portion of the width of the pocket 18. An advantage of this system is that the weight of the lower packet is spread across the width of the garment, thus providing better vertical support for the packet. The fastener strips 80 and 82 can be VELCRO brand hook and loop fasteners and/or can be provided with a plurality of cooperating snap fasteners 90A, 90B.

In the version of the invention of FIG. 5, the upper portion of the garment fabric, i.e., the shoulder portion, is made of a INTERLOCK (brand) cotton/synthetic fiber, while the main body portion of the garment is made out of an elastic garment material, such as LYCRA brand material. The pockets are made of a water resistant SUPPLEX brand material.

A garment 10 according to the present invention has significant advantages. It is slim in profile so it can easily be worn under other garments without unsightly bulges. This allows the user to have therapy throughout the working day and during physical activities.

Due to the ability to adjust the location of the lower pocket, localized heating or cooling in the lower back can be achieved, and a large number garments in various sizes do not need to be made to accommodate different sized users.

Furthermore, the packet can provide lumbar support. This feature of the invention is useful even when the packet is not heated or cooled.

Although the present invention has been described in considerable detail with reference to certain preferred versions thereof, other versions are possible. For example, a part of the inner wall of each pocket can be removed leaving a window so that direct body contact can be made with the therapeutic packet 28. Therefore, the scope of the appended claims should not be limited to the description of the preferred versions contained herein.

What is claimed is:

1. A garment adapted to be worn on a human torso for therapeutic treatment of back pain comprising:
   a) an inner layer of material forming a wearable shirt having a lower back section and an upper back section;
   b) an outer layer of material forming a pocket in the lower back section of the garment, the pocket being capable of removably receiving a packet to create a thermal change in the pocket,
   wherein the inner layer of material at the pocket is heat conductive so that the packet can alter the temperature of the lower back of the user of the garment; and
   c) means on the inner and outer layers for adjusting the distance between the pocket and the upper back section of the garment so that the garment can be used by persons of different torso length.

2. The garment of claim 1 further including a packet in the pocket.

3. The garment of claim 2 wherein the packet can be heated to a temperature higher than body temperature or cooled to a temperature lower than body temperature.

4. The garment of claim 1 wherein the outer layer in the region of the pocket is impervious to water.

5. The garment of claim 1 wherein the means for adjusting comprises a strap, first attachment means for attaching the strap to the pocket at a first location, second attachment means for attaching the strap to the garment at a second location, the second location being above the pocket, and
   wherein the elevation of at least one of the first location and the second location is adjustable.

6. The garment of claim 5 wherein the strap is fixedly attached to the pocket so that the first location is not adjustable.

7. The garment of claim 6 wherein the second attachment means comprises a snap fastener assembly having one element on the strap and a plurality of complementary elements at different elevations on the garment.

8. The garment of claim 1 including means for releasably closing the pocket after a packet is placed in the pocket.

9. The garment of claim 1 wherein the means for adjusting comprises first attachment means extending across a substantial portion of the width of the pocket, and at least two vertically spaced apart second attachment means extending across a substantial portion of the width of the garment back at locations above the pocket, the first attachment means being capable of being attached to any one of the second attachment means.

10. The garment of claim 9 wherein the first and second attachment means comprises a plurality of cooperating snap fastener portions.

11. A garment adapted to be worn on a human torso for therapeutic treatment of back pain comprising:
    a) an inner layer of material forming a wearable shirt having a lower back section and an upper back section;
    b) a lower pocket in the lower back section of the garment and at least one upper pocket in the upper back section, each pocket being capable of removably receiving a packet to create a thermal change in the pocket,
    wherein the inner layer of material at each pocket is heat conductive so that the packet can alter the temperature of the adjacent portion of the torso of the user of the garment; and
    c) means on the inner and outer layers for adjusting the distance between the lower pocket and the upper back section of the garment so that the garment can be used by persons of different torso length.

12. The garment of claim 11 wherein the means for adjusting comprises first attachment means extending across a substantial portion of the width of the pocket, and at least two vertically spaced apart second attachment means extending across a substantial portion of the width of the garment back at locations above the pocket, the first attachment means being capable of being attached to any one of the second attachment means.

* * * * *